Jan. 8, 1974 W. A. WARRINER Plant Pat. 3,432
ROSE PLANT
Filed Dec. 6, 1971
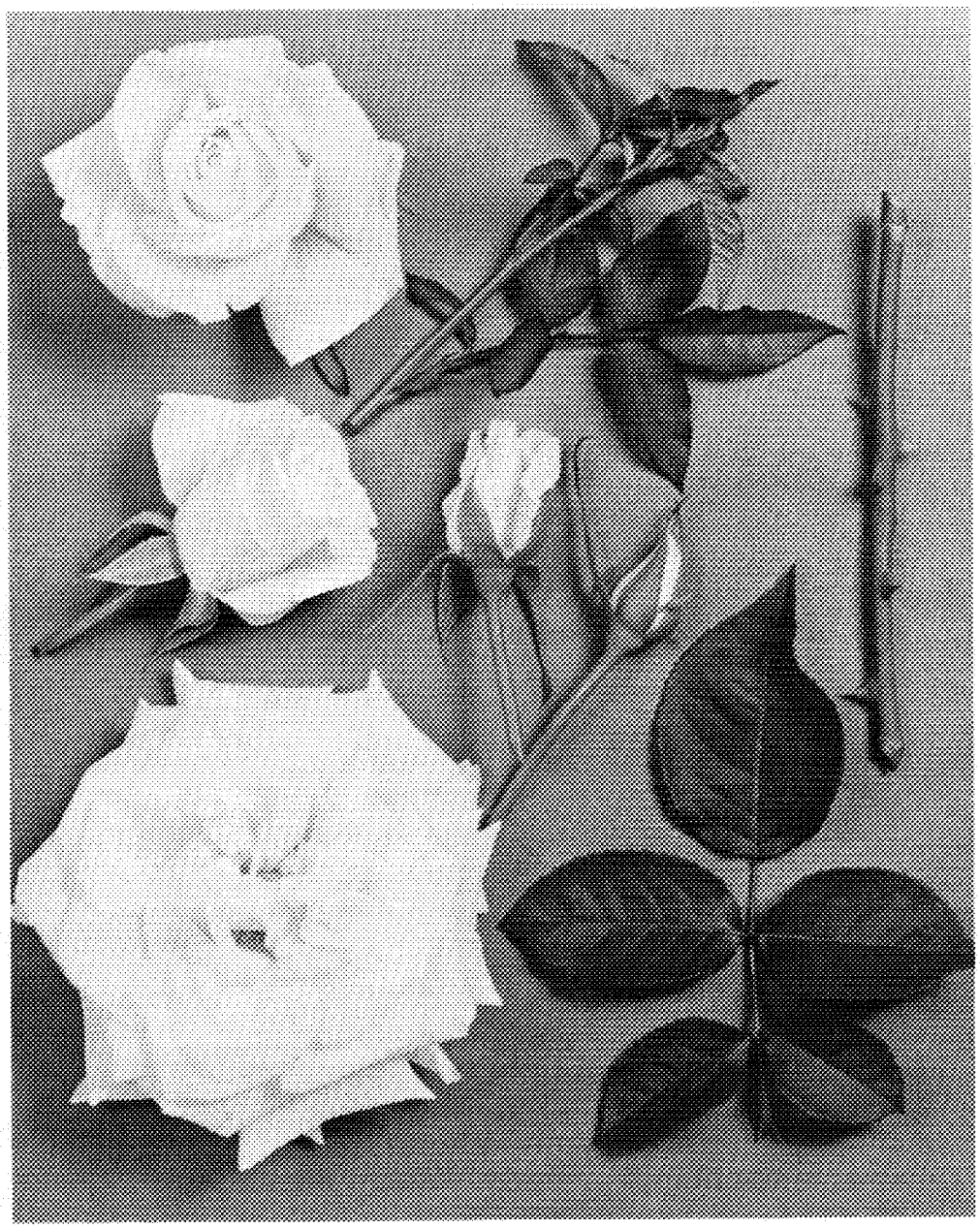
WILLIAM A. WARRINER
INVENTOR
BUCKHORN, BLORE, KLARQUIST & SPARKMAN
ATTORNEYS

United States Patent Office

Plant Pat. 3,432
Patented Jan. 8, 1974

3,432

ROSE PLANT

William A. Warriner, Tustin, Calif., assignor to Jackson & Perkins Company, Medford, Oreg.

Filed Dec. 6, 1971, Ser. No. 205,422
Int. Cl. A01h *5/00*
U.S. Cl. Plt.—14 1 Claim

The present invention relates to a new and distinct variety of rose plant, intermediate in class between hybrid tea and floribunda which was originated by me by crossing the hybrid tea variety, White Masterpiece, U.S. Plant Pat. 2,998 with the floribunda, Saratoga, U.S. plant Pat. 2,299.

The primary objective of this breeding was to produce a new rose variety similar to White Masterpiece in form and color, but of smaller size and of a more floriferous character.

This objective was substantially achieved along with other desirable improvements as evidenced by the following unique combination of characteristics which are outstanding in the new variety and which distinguish it from its parents as well as from all other varieties of which I am aware:

(1) A vigorous, well branched habit of growth, making a compact dense plant when grown outside.
(2) Year around growth when grown in a greenhouse, providing cut flowers abundantly in all months.
(3) Nearly white buds and open flowers being only lightly colored with a tint of Chartreuse Green.
(4) Foliage of unusually good quality in form and mildew resistance, being quite dark green for a white rose. New foliage is especially dark and overlaid with Garnet Brown.
(5) Little or no fragrance.

Asexual reproduction of my new variety, by budding, as performed at Wasco, Calif., shows that the foregoing characteristics and distinctions come true to form and are established and transmitted through succeeding propagations.

The accompanying drawing shows typical specimens of the vegetative growth and flowers of my new variety in different stages of development, depicted in color as true as it is reasonably possible to make the same in a color illustration of this type.

The following is a detailed description of the new rose variety with color terminology in accordance with Wilson's "Horticultural Color Chart," except where ordinary dictionary meaning is indicated.

Parentage:
- *Seed parent.*—White Masterpiece, Plant Pat. 2,998
- *Pollen parent.*—Saratoga, Plant Pat. 2,299

Classification:
- *Botanical.*—Rosa hybrid
- *Commercial.*—Intermediate between hybrid tea and floribunda

FLOWER (Observations were made in the afternoon at Irvine, Calif., in early October, of plant and flowers grown outdoors.)

Blooming habit: Recurrent—continuous

Bud:
- *Size.*—One inch when petals start to unfurl
- *Form.*—Long, pointed, ovoid, broad base
- *Color.*—When sepals first divide—Primrose Yellow 601/3) overlaid in some areas of outside petals with Chartreuse Green (663/3). When half blown; inside of petals—White, overlaid on lower area with Chartreuse Green (663/3) to (663/2) at base; reverse of petals—same as inside
- *Sepals.*—Color: Outer surface—Scheeles Green (860/3) overlaid in streaks with color near but lighter than Oxblood Red (00823/3). Inner surface—mid rib area near Pod Green (061/2), outer edges—Scheeles Green (860/3)—only lightly tomentose. Three appendaged sepals lightly appendaged. Two unappendaged sepals smooth edged
- *Receptable.*—Color: Scheeles Green (860/3). Shape: Funnel. Size: Small, broad. Surface: Smooth
- *Peduncle.*—Length: Long. Surface: Lightly prickly. Color: Light Green overlaid when older with color lighter than Garnet Brown (00918/3). Strength: Stiff, erect, heavy
- *Opening.*—Outer petals quill lightly, center petals only curve at tips slightly Bloom:
- *Size.*—Medium. Average size when fully expanded (3½" to 4")
- *Borne.*—Singly and in flat clusters
- *Stems.*—Medium, strong
- *Form.*—When first open—high center. Permanence—retains its form to the end
- *Petalage.*—Number of petals under normal conditions from 30 to 35
- *Color.*—Center of flower: Upper side of petals near White—except lower area overlaid with Chartreuse Green (663/3). Reverse side of petals—near White—same as upper side. Outer petals: Upper side of petals—near White. Reverse of petals—same. Base of petals—Chartreuse Green (663/3) or lighter. General tonality from a distance—near White, except deep in the flower color appears to be Chartreuse Green (663/3). No variegations
- *Discolorations.*—Third day: Whiter than freshly opened flower
- *Fragrance.*—Slight.

Petals:
- *Texture.*—Thick
- *Surface.*—Inside—shiny; reverse—satiny
- *Shape.*—Near round
- *Form.*—Tips slightly recurved
- *Arrangement.*—Imbricated
- *Petaloids in center.*—Few
- *Persistence.*—Drop off cleanly
- *Lastingness.*—On the plant—very long. As cut flower—long Reproductive parts:
- *Stamens, anthers.*—Medium. Color—yellow. Arrangement—regular around styles
- *Stamens, filaments.*—Color—white. Threads—medium
- *Pollen.*—Gold yellow
- *Styles.*—Loosely separated, of uneven lengths
- *Stigmas.*—Color—white
- *Ovaries.*—All enclosed in calyx

PLANT

Form: Bush

Growth: Very vigorous, upright, branching

Foliage: Compound of 5 leaflets
- *Size.*—Large
- *Quantity.*—Abundant
- *Color.*—New foliage: Under side—near Garnet Brown (00918/3). Upper side—Ivy Green (000160) overlaid with Garnet Brown (00918/3). Old foliage: Between Parsely Green (00962) and Ivy Green (0001060/3) on upper side. Near Spinach Green (0960/3) on lower side
- *Leaflets.*—Shape—Oval and oval pointed. Texture—Upper side—leathery, smooth. Under side—smooth. Ribs and veins—ordinary. Edge—Serrated. Serration—Single, small. Petiole—Rachis: Color—green. Under side—a few prickles. Stipules—Long. Disease resistance.—Very resistant to mildew under normal growing conditions at Irvine, Calif.

Wood:

*New Wood.*—Color—light green. Bark—smooth

*Old Wood.*—Color—green. Bark smooth

Thorns:

*Quantity.*—On main stalks from base—ordinary to few. On laterals from stalk—ordinary to few

*Form.*—Broad base, hooked downward

*Color when young.*—Green

*Position.*—Irregular

*Small Prickles.*—Quantity: On main stalks—few, on laterals—few. Color: Green

I claim:

1. A new and distinct variety of rose plant of a type intermediate between hybrid tea and floribunda in bush habit, flower clustering, flower size; a prolific producer of cut flowers in the greenhouse, nearly white bud and open flowers, and a strong resistance to rose powdery mildew.

No references cited.

ROBERT E. BAGWILL, Primary Examiner